(12) United States Patent
Champagne et al.

(10) Patent No.: US 10,470,994 B2
(45) Date of Patent: Nov. 12, 2019

(54) MULTIPHASIC POLYMER AS A THICKENING AND SUSPENDING AGENT

(71) Applicant: COATEX, Genay (FR)

(72) Inventors: Clementine Champagne, Caluire-et-Cuire (FR); Jean-Marc Suau, Lucenay (FR); Benoit Magny, Cailloux sur Fontaines (FR); Delphine Bony, Quincieux (FR); Yves Kensicher, Theize (FR)

(73) Assignee: COATEX, Genay (FR)

( * ) Notice: Subject to any disclaimer, the term of this patent is extended or adjusted under 35 U.S.C. 154(b) by 246 days.

(21) Appl. No.: 15/532,299

(22) PCT Filed: Oct. 30, 2015

(86) PCT No.: PCT/FR2015/052934
§ 371 (c)(1),
(2) Date: Jun. 1, 2017

(87) PCT Pub. No.: WO2016/102790
PCT Pub. Date: Jun. 30, 2016

(65) Prior Publication Data
US 2019/0021981 A1 Jan. 24, 2019

(30) Foreign Application Priority Data

Dec. 23, 2014 (FR) .................... 14 63229

(51) Int. Cl.
| | | |
|---|---|---|
| *A61K 8/81* | (2006.01) | |
| *C08F 220/06* | (2006.01) | |
| *C08F 222/10* | (2006.01) | |
| *C08F 265/06* | (2006.01) | |
| *C08L 33/08* | (2006.01) | |
| *A61Q 5/02* | (2006.01) | |
| *A61Q 19/10* | (2006.01) | |
| *A61K 8/91* | (2006.01) | |
| *C11D 3/37* | (2006.01) | |

(52) U.S. Cl.
CPC ............ *A61K 8/8152* (2013.01); *A61K 8/91* (2013.01); *A61Q 5/02* (2013.01); *A61Q 19/10* (2013.01); *C08F 220/06* (2013.01); *C08F 222/10* (2013.01); *C08F 265/06* (2013.01); *C08L 33/08* (2013.01); *C11D 3/3765* (2013.01); *A61K 2800/48* (2013.01)

(58) Field of Classification Search
CPC .... A61K 8/8152; A61K 8/91; A61K 2800/48; C08F 220/06; C08F 222/10; C08F 265/06; C08L 33/08; A61Q 5/02; A61Q 19/10

USPC ....................................................... 526/329.5
See application file for complete search history.

(56) References Cited

U.S. PATENT DOCUMENTS

| | | | |
|---|---|---|---|
| 4,309,330 A * | 1/1982 | Ukita | C08F 265/04 524/552 |
| 5,294,693 A | 3/1994 | Egraz et al. | |
| 5,362,415 A | 11/1994 | Egraz et al. | |
| 2010/0184897 A1* | 7/2010 | Dupont | C08F 265/04 524/315 |
| 2011/0207856 A1* | 8/2011 | Platel | C04B 40/0039 524/5 |
| 2012/0231056 A1* | 9/2012 | Souzy | A61K 8/068 424/401 |
| 2013/0115185 A1* | 5/2013 | Tamareselvy | A61K 8/025 424/70.16 |
| 2014/0112966 A1 | 4/2014 | Souzy et al. | |
| 2014/0179580 A1 | 6/2014 | Souzy et al. | |
| 2014/0179590 A1* | 6/2014 | Souzy | A61K 8/044 510/418 |
| 2015/0051319 A1 | 2/2015 | Platel et al. | |

OTHER PUBLICATIONS

International Search Report dated Dec. 22, 2015 in PCT/FR2015/052934 filed Oct. 30, 2015.

* cited by examiner

*Primary Examiner* — Michael Bernshteyn
(74) *Attorney, Agent, or Firm* — Oblon, McClelland, Maier & Neustadt, L.L.P.

(57) ABSTRACT

The invention relates to multiphasic polymers comprising from 45% to 95% by weight of a first polymer P1 and from 5% to 55% by weight of a second polymer P2, said polymers P1 and P2 being of distinct compositions, said polymer P1 being obtained by polymerization from a mixture of monomers comprising at least one anionic monomer (a) having a polymerizable vinyl group, at least one nonionic hydrophobic monomer (b) having a polymerizable vinyl group, at least one cross-linking monomer (c) and at least one associative monomer (d) having a polymerizable vinyl group and a hydrophobic hydrocarbon chain and said polymer P2 being obtained by polymerization from a mixture of monomers comprising at least one anionic monomer (a') having a polymerizable vinyl group, at least one nonionic hydrophobic monomer (b') having a polymerizable vinyl group and at least one cross-linking monomer (c').

It also relates to a method for the preparation of these polymers, to aqueous compositions comprising them and to their use as thickening and suspending agents.

21 Claims, No Drawings

MULTIPHASIC POLYMER AS A THICKENING AND SUSPENDING AGENT

The present invention relates to novel polymers which may be used as rheology modifying agents for aqueous formulations and make it possible to induce both good thickening and clearness properties and good suspensive performances.

Rheology modifying agents, also known as thickening or viscosity agents, are present in cleaning compositions, whether in personal care or hygiene compositions, for example cosmetic compositions, or in maintenance compositions, such as detergent products. These agents influence the rheological properties (in particular the viscosity) and the esthetic properties (such as the clearness) of the formulation, which is generally rich in surfactants, and also the ability to suspend and to stabilize particles within the formulation.

Mention may be made, among the rheology modifying agents commonly used in aqueous formulations, of polymers which are soluble or swellable in an alkaline medium, better known under the name "ASE" (for "Alkali-Soluble or Swellable Emulsions") and polymers which are soluble or swellable in an alkaline medium and which are hydrophobically modified, better known under the name "HASE" (for "Hydrophobically modified Alkali-Soluble or Swellable Emulsions"). The polymers of ASE type are linear or branched copolymers synthesized from (meth)acrylic acid and alkyl acrylates. The HASE polymers are linear or branched copolymers synthesized from (meth)acrylic acid, alkyl acrylates and at least one associative monomer.

These rheology modifying agents make it possible to access good suspensive, viscosity and clearness properties in formulations rich in surfactants having pH values close to neutrality. Unfortunately, they do not make it possible to combine, under acidic pH conditions, good suspensive, viscosity and clearness properties.

In point of fact, it is desirable to be able to formulate compositions based on surfactants within a pH range corresponding to that of the skin, that is to say at pH values of between 4 and 6, depending on whether the cosmetic product is intended for an application to the body, the face or also the mucus membranes.

Furthermore, the preservers conventionally used, such as formaldehyde donors, halogenated compounds and paraben compounds, are either prohibited from use or suspected of having harmful effects on the health. To replace them, organic acids (for example sorbic, citric or benzoic acid), as used in the food industry, are presented as an advantageous alternative. However, the antimicrobial activity of organic acids is related to the associated or protonated entities of the acid molecule. When the pH of the formulation containing the organic acid increases, salts of acids are formed by dissociation of the proton. In point of fact, the dissociated form of organic acids does not have an antimicrobial activity when it is used alone, which does not allow these organic acid compounds to be used in formulations having pH values of greater than 6.

Furthermore, it has been suggested in the literature that the formulation of products within an acidic pH range makes it possible to reduce the amount of preservers required in the product while improving its effectiveness, to stabilize and to increase the effectiveness of cosmetic active ingredients, which is beneficial in the repairing and the maintenance of the cutaneous barrier and reinforces the skin flora (Cosmetics & Toiletries®, Vol. 123, No. 12 of December 2008, "Formulating at pH 4-5: How Lower pH Benefits the Skin and Formulations").

The document WO 2012/006402 describes polymers of core-shell type comprising a linear core polymer based on acrylic units and a cross-linked shell polymer based on acrylic units. These core-shell polymers are provided in order to result in good esthetic, rheology and clearness properties in aqueous compositions comprising surfactants under acidic pH conditions. However, it appears difficult to obtain a composition incorporating the core-shell polymers described and simultaneously combining good suspensive performances, a high viscosity and a high clearness under acidic pH conditions.

The present invention is targeted at providing novel rheology modifying agents which both have good properties in terms of thickening effect (viscosity) and which make it possible to result in formulations having good suspensive performances and a high clearness (clear continuous phase), even under acidic pH conditions (pH≤6).

The inventors have discovered that it is possible to access a formulation corresponding to all of these criteria (viscosity, suspensive performances and clearness) by using, as rheology modifying agent, a specific multiphasic polymer.

More particularly, the present invention relates, according to a first of its aspects, to a multiphasic polymer comprising from 45% to 95% by weight of a first polymer, denoted P1, and from 5% to 55% by weight of a second polymer, denoted P2, the polymers P1 and P2 being of distinct compositions.

(1) Said polymer P1 being obtained by polymerization from a mixture of monomers comprising:
  at least one anionic monomer (a) having a polymerizable vinyl group,
  at least one nonionic hydrophobic monomer (b) having a polymerizable vinyl group,
  at least one cross-linking monomer (c),
  at least one associative monomer (d) having a polymerizable vinyl group and a hydrophobic hydrocarbon chain and
  optionally at least one additional nonionic monomer (e), distinct from the monomer (b).

(2) Said polymer P2 being obtained by polymerization from a mixture of monomers comprising:
  at least one anionic monomer (a') having a polymerizable vinyl group,
  at least one nonionic hydrophobic monomer (b') having a polymerizable vinyl group,
  at least one cross-linking monomer (c'),
  optionally at least one associative monomer (d') having a polymerizable vinyl group and a hydrophobic hydrocarbon chain and
  optionally at least one additional nonionic monomer (e'), distinct from the monomer (b').

Advantageously, as illustrated in the examples which follow, the multiphasic polymers according to the invention provide the formulation in which they are used with good suspensive, thickening and clearness properties, even when they are formulated at acidic pH.

A multiphasic polymer having the specific compositions P1 and P2 specified above is denoted more simply in the continuation of the text under the name "polymer according to the invention".

The expression "multiphasic polymer" is intended to denote, within the meaning of the invention, a multiphasic particle of polymer, in other words a polymer particle having a nonhomogeneous composition, prepared by a sequential polymerization method in at least two steps from at least two distinct monomer compositions.

The multiphasic particles according to the invention may in particular be structured as a core/shell, the first polymer constituting the "core" and the second polymer constituting the "shell". This "core/shell" term should not, however, be interpreted as denoting a particle in which the "core" part would be completely coated with or encapsulated by a "shell" part but as denoting a particle having a controlled morphology having two distinct phases.

The expression "polymer P1" may be understood as meaning a single polymer P1 as defined above or several polymers P1 obtained by sequential polymerization.

Likewise, the expression "polymer P2" may be understood as meaning a single polymer P2 as defined above or several polymers P2 obtained by sequential polymerization.

"Suspensive properties" or "suspending power" is intended to denote the ability of the composition to keep particles in suspension in its continuous phase, in particular in a way which is stable over time, for example during the storage of the composition.

"Particles" to be suspended is understood to mean full or hollow solid substances, liquid substances which are immiscible with the formulation or encapsulated, or gaseous substances which may be characterized by different shapes, textures, structures, compositions, colors or final properties. Mention may be made, by way of indication, of exfoliating particles (for example polyethylene particles, shells of crushed fruits, pumice), nutritious particles (for example collagen spheres), pearlescent particles (for example mica titanium, glycol distearates) and esthetic particles (for example air bubbles, flakes or pigments which are optionally colored). As regards the suspension of air bubbles in the composition, the particles may in particular have a size of 1, 2 or 3 mm.

The suspensive performances may be evaluated by observation of the stability of the suspension of standardized particles in a composition stored in a heat chamber at 45° C., as described in the examples which follow.

The "clearness" of the composition may be evaluated by measuring the transmittance of the composition. A method for determination of the transmittance is described in the examples which follow. It is expressed as percentage. A composition is regarded as clear if it has a transmittance, for a wavelength of 500 nm, of at least 60%, preferably of at least 70% and more preferably still of at least 80%.

Other characteristics, advantages and forms of application of the multiphasic polymer according to the invention will more clearly emerge on reading the description and examples which will follow, given by way of illustration and without implied limitation.

In the continuation of the text, the expressions "between . . . and . . . ", "of between . . . and . . . ", "ranging from . . . to . . . " and "varying from . . . to . . . " are equivalent and are intended to signify that the limits are included, unless otherwise mentioned.

Unless otherwise mentioned, the expression "comprising a(an)" should be understood as "comprising at least one".

Multiphasic Polymer

As indicated above, the multiphasic polymer according to the invention comprises, in particular is constituted of, from 45% to 95% by weight of a first polymer P1 and from 5% to 55% by weight of a second polymer P2, the compositions of the polymers P1 and P2 being different.

(1) Said polymer P1 being obtained by polymerization from a mixture of monomers comprising:

at least one anionic monomer (a) having a polymerizable vinyl group,
at least one nonionic hydrophobic monomer (b) having a polymerizable vinyl group,
at least one cross-linking monomer (c),
at least one associative monomer (d) having a polymerizable vinyl group and a hydrophobic hydrocarbon chain and
optionally at least one additional nonionic monomer (e), distinct from the monomer (b).

(2) Said polymer P2 being obtained by polymerization from a mixture of monomers comprising:

at least one anionic monomer (a') having a polymerizable vinyl group,
at least one nonionic hydrophobic monomer (b') having a polymerizable vinyl group,
at least one cross-linking monomer (c'),
optionally at least one associative monomer (d') having a polymerizable vinyl group and a hydrophobic hydrocarbon chain and
optionally at least one additional nonionic monomer (e'), distinct from the monomer (b').

In the continuation of the text, the proportions of monomers participating in the composition in the polymer P1 (respectively the polymer P2) are expressed as percentage by weight based on the total weight of monomers used to form the polymer P1 (respectively the polymer P2).

According to a specific embodiment, the polymer P1 does not comprise a monomer unit other than the monomers (a), (b), (c) and (d) (with the exception of the optional presence of fragments of transfer agents or of polymerization initiators).

According to a specific embodiment, the polymer P2 does not comprise a monomer unit other than the monomers (a'), (b'), (c') and (d') (with the exception of the optional presence of fragments of transfer agents or of polymerization initiators).

In other words, according to an alternative embodiment, the sum of the contents of monomers (a), (b), (c) and (d) of the composition of the polymer P1 (respectively (a'), (b'), (c') and optionally (d') of the composition of the polymer P2) is equal to 100%.

According to another alternative embodiment, the polymer P1 and/or the polymer P2 may moreover comprise one or more additional monomer unit(s) distinct from the monomers (a), (b), (c) and (d) (respectively (a'), (b'), (c') and (d')).

In particular, the composition of the polymer P1 (respectively of the polymer P2) may moreover comprise one or more nonionic additional monomer(s) (e) (respectively (e')), as described more specifically in detail in the continuation of the text.

Furthermore, it is understood that the monomers (a) and (a') (respectively (b) and (b'), respectively (c) and (c'), respectively (d) and (d'), respectively (e) and (e')) participating in the composition of the polymer P1 and of the polymer P2 may be of the same nature in the polymer P1 and in the polymer P2 or of different natures.

The monomers (a), (b), (c), (d) and (e) of the composition of the polymer P1 are different, that is to say that the monomers (a), (b), (c), (d) and (e) are distinct from one another. In particular, said monomer(s) (b) is(are) different from said monomer(s) (d). In particular, said monomer(s) (a) is(are) different from said monomer(s) (d). It is the same for the monomers (a'), (b'), (c'), (d') and (e') of the composition of the polymer P2. Thus, in particular, said monomer(s) (b')

is(are) different from said monomer(s) (d'). In particular, said monomer(s) (a') is(are) different from said monomer(s) (d').

According to a specific embodiment, the polymer P1/polymer P2 weight ratio of the multiphasic polymer according to the invention is between 45/55 and 95/5, in particular between 60/40 and 95/5.

Anionic Monomer Having a Polymerizable Vinyl Group

According to a specific embodiment, the anionic monomers (a) and (a') having a polymerizable vinyl group, referred to more simply in the continuation of the text as "anionic monomers", comprise at least one carboxyl group.

In particular, the anionic monomers may be chosen from acrylic acid, methacrylic acid, maleic acid, itaconic acid, crotonic acid and their mixtures, and/or the salts of these acids.

According to a specific embodiment, the anionic monomers may be chosen from acrylic acid and/or methacrylic acid monomers and/or one of their salts.

Preferably, the anionic monomer (a) of the polymer P1 and (a') of the polymer P2 of the multiphasic polymer according to the invention is methacrylic acid (MAA).

Said anionic monomer(s) (a) may represent from 20% to 53% by weight, in particular from 25% to 48% by weight and more particularly from 30% to 43% by weight, based on the total weight of monomers constituting the polymer P1.

Said anionic monomer(s) (a') may represent from 10% to 53% by weight, in particular from 15% to 48% by weight and more particularly from 20% to 43% by weight, based on the total weight of monomers constituting the polymer P2.

Said anionic monomer(s) (a) and (a') may represent from 14.5% to 53% by weight, in particular from 19.5% to 48% by weight and more particularly from 24.5% to 43% by weight, of the total weight of monomers constituting the multiphasic polymer of the invention.

Nonionic Hydrophobic Monomer Having a Polymerizable Vinyl Group

The nonionic hydrophobic monomers (b) and (b') having a polymerizable vinyl group, referred to more simply in the continuation of the text as "nonionic hydrophobic monomers", are monomers having neither a positive charge nor a negative charge in aqueous solution.

They may be chosen from esters, amides or nitriles of acrylic or methacrylic acids or from acrylonitrile, styrene, methylstyrene, diisobutylene, vinylpyrrolidone or vinylcaprolactam.

Very particularly, the nonionic hydrophobic monomers may be chosen from $C_1$-$C_8$ alkyl acrylates or $C_1$-$C_8$ alkyl methacrylates, such as methyl acrylate, ethyl acrylate, butyl acrylate, 2-ethylhexyl acrylate, methyl methacrylate, ethyl methacrylate, butyl methacrylate and their mixtures.

According to a specific embodiment, the nonionic hydrophobic monomers may be chosen from ethyl acrylate, butyl acrylate, ethyl methacrylate and their mixtures.

In particular, the nonionic hydrophobic monomer (b) of the polymer P1 and (b') of the polymer P2 of the multiphasic polymer according to the invention may be ethyl acrylate (EA).

Said nonionic hydrophobic monomer(s) (b) may represent from 40% to 75% by weight, in particular from 45% to 70% by weight and more particularly from 50% to 65% by weight, based on the total weight of monomers constituting the polymer P1.

Said nonionic hydrophobic monomer(s) (b') may represent from 50% to 85% by weight, in particular from 55% to 80% by weight and more particularly from 60% to 75% by weight, based on the total weight of monomers constituting the polymer P2.

Said nonionic hydrophobic monomer(s) (b) and (b') may represent from 40% to 83% by weight, in particular from 45% to 78% by weight and more particularly from 50% to 73% by weight of the total weight of monomers constituting the multiphasic polymer of the invention.

According to a particularly preferred embodiment, the mass proportion of monomers (b') in the polymer P2 (mass content of monomers (b') based on the total weight of monomers constituting the polymer P2) is greater than that in the polymer P1 (mass content of monomers (b) based on the total weight of monomers constituting the polymer P1).

Said anionic monomer(s) (a) and (a') and said nonionic hydrophobic monomer(s) (b) and (b') may represent more than 83% by weight, in particular between 83% and 99.3% by weight of the overall composition of the multiphasic polymer of the invention.

"Overall composition" is understood to mean the total weight of the monomers used for the synthesis of the multiphasic polymer.

Preferably, the nonionic hydrophobic monomers (b')/anionic monomers (a') weight ratio of the composition of the polymer P2 is between 60/40 and 85/15, in particular between 65/35 and 80/20.

According to a specific embodiment, the nonionic hydrophobic monomers (b)/anionic monomers (a) weight ratio of the composition of the polymer P1 is between 53/47 and 70/30, in particular between 55/45 and 68/32.

According to a specific embodiment, the multiphasic polymer according to the invention is such that:
  the anionic monomers (a) and (a') of the polymers P1 and P2 are chosen from acrylic acid and/or methacrylic acid and/or one of their salts; in particular, the monomer (a) and the monomer (a') are methacrylic acid and
  the nonionic hydrophobic monomers (b) and (b') of the polymers P1 and P2 are chosen from ethyl acrylate, butyl acrylate, ethyl methacrylate or their mixtures; in particular, the monomer (b) and the monomer (b') are ethyl acrylate.

Cross-Linking Monomer

The polymer P1 and the polymer P2 of the multiphasic polymer according to the invention are partially or completely cross-linked.

The compositions of the polymer P1 and of the polymer P2 thus both comprise, in addition, one or more cross-linking monomer(s).

According to a specific embodiment, the multiphasic polymer according to the invention comprises a single cross-linking monomer. According to another embodiment, it comprises two different cross-linking monomers. The cross-linking monomer(s) is(are) used to generate a polymer in the form of three-dimensional network.

According to the present invention, use is made, as cross-linking monomer, of a monomer which is a polyunsaturated compound. This compound may comprise two, three or several ethylenic unsaturations.

The cross-linking monomer may have a hydrophilic, hydrophobic or amphiphilic nature. Examples of these compounds include di(meth)acrylate compounds, such as polyalkylene glycol di(meth)acrylate, in particular polypropylene glycol di(meth)acrylate, ethylene glycol di(meth)acrylate, polyethylene glycol di(meth)acrylate, triethylene glycol di(meth)acrylate, 1,3-butylene glycol di(meth)acrylate, 1,6-butylene glycol di(meth)acrylate, 1,6-hexanediol di(meth)acrylate, neopentyl glycol di(meth)acrylate or 1,9- nonanediol di(meth)acrylate, but also 2,2'-bis(4-(acryloxypropyloxy)-phenyl)propane, 2,2'-bis(4-(acryloxydiethoxy)-phenyl)propane and zinc acrylate; tri(meth)acrylate compounds, such as trimethylolpropane tri(meth)acrylate, trimethylolethane tri(meth)acrylate, pentaerythritol tri (meth)acrylate and tetramethylolmethane tri(meth)acrylate; tetra(meth)acrylate compounds such as ditrimethylolpropane tri(meth)acrylate, tetramethylolmethane tetra(meth) acrylate and pentaerythritol tetra(meth)acrylate; hexa(meth) acrylate compounds, such as dipentaerythritol hexa(meth) acrylate; penta(meth)acrylate compounds, such as dipentaerythritol penta(meth)acrylate; allyl compounds, such as allyl (meth)acrylate, diallyl phthalate, diallyl itaconate, diallyl fumarate and diallyl maleate; polyallyl ethers of sucrose having from 2 to 8 groups per molecule, polyallyl ethers of pentaerythritol, such as pentaerythritol diallyl ether, pentaerythritol triallyl ether and pentaerythritol tetraallyl ether; or polyallyl ethers of trimethylolpropane, such as trimethylolpropane diallyl ether and trimethylolpropane triallyl ether. Other polyunsaturated compounds include divinyl glycol, divinylbenzene, divinylcyclohexane and methylenebisacrylamide. According to another aspect, the cross-linking monomers may be prepared by an esterification reaction of a polyol with an unsaturated anhydride, such as maleic anhydride or itaconic anhydride, or by an addition reaction with an isocyanate, such as (3-isopropenyl)dimethylbenzene isocyanate.

Use may also be made of the following compounds in order to obtain cross-linking monomers: polyhaloalkanols, such as 1,3-dichloroisopropanol and 1,3-dibromoisopropanol; haloepoxyalkanes, such as epichlorohydrin, epibromohydrin, 2-methylepichlorohydrin and epiiodohydrin; polyglycidyl ethers, such as 1,4-butanediol diglycidyl ether, glycerol 1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ether, bisphenol A epichlorohydrin epoxy resin and mixtures.

According to a specific embodiment, the cross-linking monomers used in the polymer P1 and in the polymer P2 are chosen from trifunctional cross-linking agents.

It may in particular be trimethylolpropane triacrylate (TMPTA).

The content of cross-linking monomer(s) (c) in the composition of the polymer P1 may more particularly be greater than or equal to 0.3% by weight, based on the total weight of the monomers constituting the polymer P1, in particular greater than or equal to 0.4% by weight and preferably between 0.4% and 5% by weight.

The content of cross-linking monomer(s) (c') in the composition of the polymer P2 may more particularly be greater than or equal to 0.2% by weight, based on the total weight of the monomers constituting the polymer P2, in particular greater than or equal to 0.3% and especially between 0.3% and 5% by weight.

Said cross-linking monomer(s) (c) and (c') may represent from 0.2% to 5% by weight, in particular from 0.3% to 5% by weight, of the total weight of monomers constituting the multiphasic polymer of the invention.

Associative Monomer

The associative monomers having a polymerizable vinyl group and a hydrophobic hydrocarbon chain are preferably chosen from alkoxylated monomers. They may more particularly be chosen from monomers of following formula (I):

$$T-[(EO)_n(PO)_{n'}(BO)_{n''}]-Z \qquad (I)$$

in which:
T represents an end making possible the copolymerization of the associative monomer,
$[(EO)_n(PO)_{n'}(BO)_{n''}]$ represents a polyalkoxylated chain consisting of alkoxylated units, distributed in blocks, alternating or random, chosen from ethoxylated units EO, propoxylated units PO and butoxylated units BO,
n, n' and n" represent, independent of one another, 0 or an integer varying from 1 to 150 and
Z represents a linear or branched fatty chain of at least 12 carbon atoms and optionally comprising one or more 5- to 7-membered cyclic group(s) which are saturated, partially unsaturated or aromatic; said groups may be optionally substituted.

Equivalently, the associative monomer may be represented according to the following formula (II):

$$T-A-Z \qquad (II)$$

in which:
T represents an end making possible the copolymerization of the associative monomer,
A represents a polymer chain consisting of:
m alkylene oxide units of formula —$CH_2CHR_1O$— with $R_1$ representing an alkyl group comprising from 1 to 4 carbons, for example a methyl or ethyl group, and m varying from 0 to 150,
p alkylene oxide units of formula —$CH_2CHR_2O$— with $R_2$ representing an alkyl group comprising from 1 to 4 carbons, for example a methyl or ethyl group, and p ranging from 0 to 150,
n ethylene oxide units with n varying from 0 to 150, or from 10 or 15 to 150, or from 10 or 15 to 100, or from 15 to 50, or from 15 to 30, in which m+n+p≥0 and
in which the alkylene oxide units of formula —$CH_2CHR_1O$—, the alkylene oxide units of formula —$CH_2CHR_2O$— and the ethylene oxide units are in blocks, alternating or random, and
Z is as defined above.

"Propoxylated units PO" and "butoxylated units BO" are understood to mean ethoxylated units carrying, on one or other of their carbons, a methyl or ethyl radical respectively. An ethoxylated unit is a —$CH_2$—$CH_2$—O unit.

"Fatty chain" is understood to mean a linear or branched aliphatic hydrocarbon chain of a fatty acid comprising at least 12 carbon atoms, or from 12 to 36 carbon atoms, or from 12 to 32 carbon atoms.

The Z chain may comprise, for example, from 2 to 10 aromatic cyclic groups.

According to a specific embodiment, the fatty chain Z may comprise one or more phenol group(s) carrying one or more styryl group(s), such as, for example, distyrylphenol, tristyrylphenol and/or pentastyrylcumylphenol groups.

Preferably, the Z chain is a branched chain comprising 16 carbon atoms.

The end T more particularly represents a radical containing a polymerizable unsaturated group belonging to the group of the acrylic, methacrylic, maleic, itaconic orcrotonic esters. The end T may be chosen in particular from acrylate, methacrylate, allyl, vinyl, methacrylurethane and α,α-dimethyl-m-isopropenylbenzylurethane groups.

According to a specific embodiment, the associative monomer corresponds to the formula (III):

$$CH_2=C(R_1)-COO-[(EO)_n(PO)_{n'}(BO)_{n''}]-Z \qquad (III)$$

in which:
R₁ represents H or CH₃ and
n, n', n" and Z have the same definition as in the above formula (I).

Equivalently, the associative monomer corresponds to the following formula (IV):

CH₂=C(R₁)—COO-A-Z          (IV)

in which:
R₁ represents H or CH₃ and
A and Z have the same definition as in the above formula (II).

According to a specific embodiment, n' and n" in the abovementioned formula (I) or (III) are zeros and n preferably varies from 15 to 150, in particular from 15 to 50 and especially from 15 to 30. In other words, A in the abovementioned formulae (II) and (IV) represents a polymeric chain consisting of 15 to 150, in particular of 15 to 50 and especially of 15 to 30 ethylene oxide units.

By way of example, the associative monomer may correspond to the formula (III) in which n' and n" are zeros, n has a value of 25, R₁ represents CH₃ and Z is a branched chain comprising 16 carbon atoms.

As indicated above, said associative monomer(s) may be present solely in the polymer P1.

Alternatively, said associative monomer(s) may be present both in the polymer P1 and in the polymer P2 of the multiphasic polymer of the invention.

Said associative monomer(s) (d), and optionally (d'), may represent at least 0.5% by weight of the overall composition of the multiphasic polymer of the invention.

"Overall composition" is understood to mean the total weight of the monomers used for the synthesis of the multiphasic polymer.

In particular, said associative monomer(s) (d) may be used in a proportion of at least 0.5% by weight, in particular from 0.5 to 12% by weight, based on the total weight of monomers constituting the polymer P1.

Additional Nonionic Monomers

The polymers P1 and P2 may comprise one or more additional nonionic monomer(s) (e) and/or (e'). These additional nonionic monomers (e) and (e') may more particularly be chosen from:
2-acrylamido-2-methylpropanesulfonic acid (AMPS),
unsaturated telomers of acrylic acid,
the monomers of formula (e1):

(e1)

in which:
R_a, R_b and R_c represent, independently of one another, H or CH₃,
n is an integer equal to 1 or to 2 and
the monomers of formula (e2):

(e2)

in which:
$R_{a'}$, $R_{b'}$, $R_{c'}$ and $R_{d'}$ represent, independently of one another, H or CH₃,
X represents (C=O) or (CH₂), with r=0, 1 or 2,
(AO) represents a polyalkoxylated chain consisting of alkoxylated units, distributed in blocks, alternating or random, chosen from ethoxylated units EO, propoxylated units PO and butoxylated units BO and
q represents 0 or an integer varying from 1 to 150.

In particular, the additional monomers of formula (e1) may be chosen from allyl alcohol (n=1), methallyl alcohol (n=1) and isoprenol (n=2). Advantageously, the optional monomer is isoprenol.

"Unsaturated telomers of acrylic acid" is understood to mean oligomers of acrylic acid or of acryloyloxypropionic acid, of formula (V):

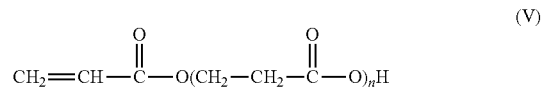

(V)

where n is an integer varying from 1 to 10. These different oligomers may be as a mixture. When n=1, the oligomer is an acrylic acid dimer.

It is understood that the different specific embodiments described for each of the anionic, nonionic hydrophobic, cross-linking and associative monomers of the multiphasic polymer according to the invention may be combined.

Said additional nonionic monomer(s) (e) and (e') may represent less than 50% by weight of the overall composition of the multiphasic polymer of the invention, in particular less than 40% by weight and more particularly from 1% to 30% by weight.

According to a particularly preferred embodiment, the multiphasic polymer according to the invention consists:
(1) of a polymer P1 obtained by polymerization from a mixture of monomers comprising, indeed even being constituted of:
from 30% to 43% by weight of at least one anionic monomer (a) having a polymerizable vinyl group,
from 50% to 65% by weight of at least one nonionic hydrophobic monomer (b) having a polymerizable vinyl group,
from 0.4% to 5% by weight of at least one cross-linking monomer (c),
at least 0.5% by weight of at least one associative monomer (d) having a polymerizable vinyl group and a hydrophobic hydrocarbon chain and
optionally at least one additional nonionic monomer (e), distinct from the monomer (b) and
(2) of a polymer P2 obtained by polymerization from a mixture of monomers comprising, indeed even being constituted of:
from 20% to 43% by weight of at least one anionic monomer (a') having a polymerizable vinyl group,
from 60% to 75% by weight of at least one nonionic hydrophobic monomer (b') having a polymerizable vinyl group,
from 0.3% to 5% by weight of at least one cross-linking monomer (c'),
optionally at least one associative monomer (d') having a polymerizable vinyl group and a hydrophobic hydrocarbon chain and
optionally at least one additional nonionic monomer (e'), distinct from the monomer (b').

According to a specific embodiment, the multiphasic polymer according to the invention is obtained from at least the following monomers:
- one or more anionic monomer(s) chosen from acrylic acid and/or methacrylic acid and/or one of their salts, in particular methacrylic acid,
- one or more nonionic hydrophobic monomer(s) chosen from ethyl acrylate, butyl acrylate, ethyl methacrylate or their mixtures, in particular ethyl acrylate,
- one or more cross-linking monomer(s), in particular as defined above and more particularly trimethylolpropane triacrylate,
- one or more associative monomer(s) of abovementioned formula (II) or (III), in particular of abovementioned formula (IV) or (V) and more particularly as described above and
- optionally one or more additional nonionic monomer(s) as defined above.

Preparation of the Multiphasic Polymer According to the Invention

The multiphasic polymers according to the invention may be prepared sequentially by an emulsion, dispersion or solution radical polymerization method.

Preferably, they are prepared by radical polymerization in at least two steps, the polymer P1 and the polymer P2 being produced in two sequential emulsion polymerization steps, in particular in this order P1 then P2.

The polymerization is carried out in appropriate solvents, in the presence of known initiators.

By way of example, the polymerization initiator may be a persulfate salt, such as ammonium persulfate.

The emulsion radical polymerization may advantageously be carried out in the presence of at least one surfactant and optionally of at least one chain transfer agent, making it possible to regulate the molecular mass of the chains produced during the polymerization.

Mention may be made, as surfactants liable to be used, of anionic surfactants, such as a fatty acid salt, an alkyl sulfate salt (such as sodium lauryl sulfate), an alkyl ether sulfate salt (such as sodium lauryl ether sulfate), an alkylbenzenesulfonate salt (such as sodium dodecylbenzenesulfonate), an alkyl phosphate salt or a sulfosuccinate diester salt, nonionic surfactants, such as a polyoxyethylene alkyl ether or a polyoxyethylene fatty acid ester, cationic surfactants, such as quaternary alkyl- and/or arylammonium halides, or zwitterionic or amphoteric surfactants, such as the surfactants comprising a betaine group.

Mention may advantageously be made, as chain transfer agents, of mercaptan compounds comprising at least four carbon atoms, such as butyl mercaptan, n-octyl mercaptan, n-dodecyl mercaptan or tert-dodecyl mercaptan.

The emulsion polymerization is carried out conventionally in an aqueous dispersion medium.

Thus, the invention is targeted more particularly at a method for the preparation of a multiphasic polymer according to the invention, comprising at least the following consecutive steps:
(i) polymerization of the polymer P1 from a first mixture of monomers comprising:
- at least one anionic monomer (a) having a polymerizable vinyl group,
- at least one nonionic hydrophobic monomer (b) having a polymerizable vinyl group,
- at least one cross-linking monomer (c),
- at least one associative monomer (d) having a polymerizable vinyl group and a hydrophobic hydrocarbon chain and
- optionally at least one additional nonionic monomer (e), distinct from the monomer (b), and
(ii) polymerization in the presence of the polymer P1 obtained above of a second mixture of monomers comprising:
- at least one anionic monomer (a') having a polymerizable vinyl group,
- at least one nonionic hydrophobic monomer (b') having a polymerizable vinyl group,
- at least one cross-linking monomer (c'),
- optionally an associative monomer (d') having a polymerizable vinyl group and a hydrophobic hydrocarbon chain and
- optionally an additional nonionic monomer (e'), distinct from the monomer (b').

From a practical viewpoint, the first step consists in bringing the monomers intended to participate in the composition of the polymer P1 into contact with a polymerization initiator, it being possible for this contacting operation to be carried out batchwise or semicontinuously (the contacting operation being carried out over a period of time which may range from several minutes to several hours).

From a practical viewpoint, the second step (step of producing the polymer P2) may take place in the following way:
- a step of addition of the monomers intended to participate in the composition of the polymer P2 to a dispersion medium comprising the preformed polymer P1, it being possible for this addition to be carried out batchwise or semicontinuously (the contacting operation being carried out over a period of time which may range from several minutes to several hours) and
- simultaneously for the semicontinuous mode or subsequent to this addition step for the batchwise mode, a step of introduction of a polymerization initiator.

Applications

The multiphasic polymers according to the invention prove to be particularly effective as rheology modifying agents in a wide range of aqueous compositions, in particular washing compositions including surfactants, such as care compositions or maintenance compositions. The expression "care compositions" comprises, for example, cosmetic compositions, personal hygiene compositions, toiletries and cleaning compositions for application to the body (including the skin, the hair, the nails) of humans or animals, for example shampooing compositions. The expression "maintenance compositions" includes the compositions used for cleaning or the maintenance of sanitary conditions, for example in the kitchen or the bathroom, detergent products, laundry products, etc.

The invention thus relates, according to yet another of its aspects, to an aqueous composition comprising at least one multiphasic polymer according to the invention or as obtained according to the method described above.

The multiphasic polymer according to the invention may be used in the aqueous composition in a proportion of 0.1% to 20% by weight, in particular of 0.5% to 12% by weight, based on the total weight of the composition.

As illustrated in the examples which follow, the polymer according to the invention makes it possible to advantageously combine performances in terms of thickening effect, of clearness and of suspensive properties. In other words, it makes it possible to obtain an aqueous composition having the desired viscosity and comprising a clear continuous phase and suspended particles homogeneously distributed in the continuous phase.

The invention thus more particularly relates to the use of a multiphasic polymer according to the invention in an aqueous composition as a thickening and suspending agent.

It also relates to the use, for the preparation of a stable aqueous composition comprising a clear continuous phase and suspended particles distributed in the continuous phase, preferably with a pH of less than or equal to 6, of a multiphasic polymer as defined above.

The invention also relates to an agent for obtaining a stable aqueous composition, comprising a clear continuous phase and suspended particles distributed in the continuous phase, in particular with a pH of less than or equal to 6, comprising a multiphasic polymer according to the invention.

In addition to the clearness which it contributes, the agent of the invention thus makes it possible to keep suspended the particles present in the composition. The use of a composition thus formulated therefore does not require any mixing step, even if the composition has been stored for several weeks, indeed several months.

A composition according to the invention may comprise ingredients conventionally used in the abovementioned formulations. It may comprise one or more active ingredient(s) (or active agent(s)) under any form whatsoever and whatever the field of application of the composition, as indicated above. The active principle(s) may be dissolved in the continuous phase of the composition and/or they may be in particulate form, insoluble in the continuous phase, and constitute all or a portion of the suspended particles.

It may comprise one or more surfactant(s), in particular chosen from anionic, zwitterionic or amphoteric, cationic or nonionic surfactants and their mixtures.

The invention more particularly relates to an aqueous cosmetic composition comprising a continuous phase and suspended particles in the continuous phase, said continuous phase and/or said particles comprising and/or consisting of a cosmetic active principle, said composition comprising a multiphasic polymer as defined above.

It may comprise, as active principle(s), a washing base for the body and/or hair.

Advantageously, the rheology modifying agent according to the invention makes it possible to access the desired properties of viscosity, of clearness and of suspensive effect for a wide pH range, in particular when it is formulated in compositions with a pH of less than or equal to 6, in particular of less than or equal to 5.5, in particular of less than or equal to 5 and especially of between 4 and 5.

Such pH values are close to the mean pH value of human skin. The rheology modifying agent according to the invention is thus of major advantage in cosmetics.

The invention will now be described by means of the following examples, given, of course, by way of illustration and without limitation of the invention.

EXAMPLES

The following abbreviations are used:
MAA: (meth)acrylic acid.
EA: ethyl acrylate.
AM: associative monomer of formula (IV) in which n' and n" are zeros, n has a value of 25, $R_1$ represents $CH_3$ and Z is a branched chain comprising 16 carbon atoms.
TMPTA: trimethylolpropane triacrylate.
Synthesis of the Multiphasic Polymers The protocol for the synthesis of the multiphasic polymer denoted "Pol.1" of example 1 is as follows:

430 g of water and 4.65 g of sodium lauryl ether sulfate (28% Texapon NSO) are introduced into a stirred 1l reactor heated using an oil bath.

The premix comprising the monomers corresponding to the polymer P1 is prepared in a beaker. It contains 141.0 g of water, 4.9 g of 28% Texapon NSO, 82.5 g of MAA, 131.7 g of EA, 19.3 g of AM and 2.1 g of TMPTA.

The premix comprising the monomers corresponding to the polymer P2 is prepared in a second beaker. It contains 43.4 g of water, 1.5 g of 28% Texapon NSO, 26.9 g of MAA, 54.8 g of EA, 6.0 g of AM and 0.7 g of TMPTA.

The solution of polymerization initiator is prepared in a third beaker. The solution contains 0.587 g of ammonium persulfate and 55 g of water.

The solution of polymerization initiator is injected over 2 hours and the premix of monomers corresponding to the polymer P1 is injected over 1 hour 30 minutes, in parallel, into the reactor maintained at 86±2° C., followed by the premix of monomers corresponding to the polymer P2 over 30 minutes.

This polymerization step is followed by the injection, over 1 hour, of a mixture containing 0.1 g of ammonium persulfate and 35 g of water.

The combined mixture is subsequently cooled to ambient temperature.

All of the multiphasic polymers presented in the examples which follow were synthesized under the conditions described above, the compositions of monomers and the injection times of the premixes of monomers being varied.

The composition of the polymer P1 (respectively of the polymer P2) is shown therein as percentage by weight of each of the monomers, based on the total weight of the monomers of P1 (respectively of P2).

Evaluation in an Aqueous Formulation

The polymers are tested in an aqueous formulation, with the composition shown in the following table 1 (2% or 2.4% by weight of multiphasic polymer, based on the total weight of the composition).

TABLE 1

| Compounds | Amount (% by weight) |
|---|---|
| Sodium lauryl ether sulfate | 9 |
| Cocamidopropyl betaine | 3 |
| Polymer tested | 2 or 2.4 |
| Water | q.s.f 100 |

The pH of the formulation is adjusted to a value of 4, 5 or 6 by addition of lactic acid or of sodium hydroxide.

Properties Evaluated

The compositions are evaluated for their properties of clearness, of viscosity and of suspensive performances.

Clearness

The clearness of the composition is evaluated by measurement of the transmittance according to the following protocol:

The measurements are carried out on a Genesys 10 UV™ UV spectrometer (Cole Parmer), equipped with Rotilabo-Einmal Kuvetten PS, 4.5 ml, cells. In practice, the apparatus is preheated 10 minutes before use. A first measurement is first carried out using a cell filled with 3.8 ml of bi-permuted water (the "blank"). The measurement is subsequently carried out with a cell filled with 3.8 ml of the solution of cosmetic composition to be tested. The transmittance is then measured at the wavelength of 500 nm. The higher the transmittance value, expressed as percentage, the clearer the cosmetic composition.

As indicated above, it is considered that, at a transmittance value at 500 nm of at least 60%, the composition is clear.

Viscosity

The viscosity of said formulations is measured using a Brookfield viscometer, model LVT. Before the measurement of the viscosity, each of the formulations is left standing at 25° C. for 24 hours. The spindle has to be centered with respect to the opening of the flask.

The viscosity is subsequently measured at 6 rpm using the appropriate module. The viscometer is allowed to rotate until the viscosity is stable.

The rheology modifying agent has to contribute a sufficient viscosity to the formulation in which it is used. Generally, the viscosity desired for thickened formulations is greater than 2000 mPa·s, in particular greater than 3000 mPa·s and more particularly greater than 4000 mPa·s.

Suspensive Performances

The suspensive performances are evaluated by observation of the stability of polyethylene beads with a diameter of 800 μm in the cosmetic formulation after storage in a heat chamber at 45° C.

As soon as a displacement of particles is recorded, the test is halted. The results are graded as follows:

| Stability time | Suspension grade |
| --- | --- |
| Up to 7 days | 1 |
| Up to 30 days | 2 |
| Up to 60 days | 3 |
| Up to 75 days | 4 |
| More than 90 days | 5 |

It is considered that the suspensive performances of the formulation are satisfactory for a duration of stability of at least 75 days, i.e. a suspension grade≥4.

Example 1

Influence of the Presence of the Cross-Linking Monomer in the Polymer P1 and in the Polymer P2

TABLE 2

| Polymer tested | | Pol. 1 | C1 (outside the invention) |
| --- | --- | --- | --- |
| Composition P1 | EA | 55.92 | 56.42 |
| | MAA | 35.00 | 35.31 |
| | AM | 8.19 | 8.26 |
| | TMPTA | 0.89 | 0.00 |

TABLE 2-continued

| Polymer tested | | Pol. 1 | C1 (outside the invention) |
| --- | --- | --- | --- |
| Composition P2 | EA | 62.01 | 62.01 |
| | MAA | 30.50 | 30.50 |
| | AM | 6.76 | 6.76 |
| | TMPTA | 0.74 | 0.74 |
| Overall composition | EA | 57.58 | 57.95 |
| | MAA | 33.77 | 33.99 |
| | AM | 7.80 | 7.85 |
| | TMPTA | 0.85 | 0.20 |
| Proportion P1 | | 72.74 | 72.56 |
| Proportion P2 | | 27.26 | 27.44 |
| 2.4% active agent, pH = 5 | Brook Visco (mPa · s) | 17,400 | 12,600 |
| | Suspension grade | 5 | 3 |
| | T (500 nm) (%) | 87 | 93 |

TABLE 3

| Polymer tested | | Pol. 2 | C2 (outside the invention) |
| --- | --- | --- | --- |
| Composition P1 | EA | 55.92 | 55.92 |
| | MAA | 35.00 | 35.00 |
| | AM | 8.19 | 8.19 |
| | TMPTA | 0.89 | 0.89 |
| Composition P2 | EA | 62.01 | 62.47 |
| | MAA | 30.50 | 30.72 |
| | AM | 6.76 | 6.81 |
| | TMPTA | 0.74 | 0.00 |
| Overall composition | EA | 57.58 | 57.69 |
| | MAA | 33.77 | 33.84 |
| | AM | 7.80 | 7.82 |
| | TMPTA | 0.85 | 0.65 |
| Proportion P1 | | 72.74 | 72.88 |
| Proportion P2 | | 27.26 | 27.12 |
| Brook Visco at 2% active agent (mPa · s) | pH = 4 | 8,400 | 7,100 |
| | pH = 5 | 7,400 | 6,500 |
| | pH = 6 | 5,800 | 4,900 |
| Suspension grade at 2% active agent | pH = 4 | 5 | 3 |
| | pH = 5 | 5 | 2 |
| | pH = 6 | 4 | 2 |
| T (500 nm) at 2% active agent (%) | pH = 4 | 82 | 81 |
| | pH = 5 | 84 | 85 |
| | pH = 6 | 91 | 90 |

The results presented in tables 2 and 3 show that the presence of the cross-linking monomer both in the polymer P1 and in the polymer P2 makes it possible to access an improved viscosity and improved suspensive properties, while retaining the desired properties of clearness.

Example 2

Influence of the Presence of the Associative Monomer in the Multiphasic Polymer

TABLE 4

| Polymer tested | | Pol. 2 | C3 (outside the invention) | Pol. 3 | Pol. 4 | C4 (outside the invention) |
| --- | --- | --- | --- | --- | --- | --- |
| Composition P1 | EA | 55.92 | 60.91 | 55.92 | 54.53 | 66.58 |
| | MAA | 35.00 | 38.12 | 35.00 | 34.14 | 32.36 |
| | AM | 8.19 | 0.00 | 8.19 | 10.46 | 0.00 |
| | TMPTA | 0.89 | 0.97 | 0.89 | 0.87 | 1.06 |
| Composition P2 | EA | 62.01 | 63.30 | 66.50 | 66.50 | 43.44 |
| | MAA | 30.50 | 35.95 | 32.71 | 32.71 | 35.99 |
| | AM | 6.76 | 0.00 | 0.00 | 0.00 | 20.05 |
| | TMPTA | 0.74 | 0.75 | 0.79 | 0.79 | 0.52 |

TABLE 4-continued

| Polymer tested | | Pol. 2 | C3 (outside the invention) | Pol. 3 | Pol. 4 | C4 (outside the invention) |
|---|---|---|---|---|---|---|
| Overall composition | EA | 57.58 | 61.59 | 58.66 | 57.57 | 57.58 |
| | MAA | 33.77 | 37.50 | 34.41 | 33.77 | 33.77 |
| | AM | 7.80 | 0.00 | 6.07 | 7.80 | 7.80 |
| | TMPTA | 0.85 | 0.91 | 0.86 | 0.85 | 0.85 |
| Proportion P1 | | 72.74 | 71.44 | 74.11 | 74.58 | 61.09 |
| Proportion P2 | | 27.26 | 28.56 | 25.90 | 25.42 | 38.91 |
| Brook Visco at 2% active agent (mPa·s) | pH = 4 | 8,400 | 2,800 | 7,300 | 7,200 | 12,200 |
| | pH = 5 | 7,400 | 2,400 | 6,100 | 6,200 | 10,800 |
| Suspension grade at 2% active agent | pH = 4 | 5 | 1 | 4 | 4 | 1 |
| | pH = 5 | 4 | 1 | 4 | 4 | 1 |
| T (500 nm) at 2% active agent (%) | pH = 4 | 82 | 85 | 82 | 81 | 93 |
| | pH = 5 | 84 | 85 | 83 | 81 | 94 |

It emerges from the results presented in table 4 that the absence of associative monomer in the polymer P1 does not make it possible to access good suspensive performances.

On the other hand, the presence of associative monomer according to the invention in the polymer P1 and optionally, in addition, in the polymer P2 of the multiphasic polymer results in good properties simultaneously in terms of viscosity, of transmittance and of suspensive performances.

Example 3

Influence of the Multiphasic Structure According to the Invention

The polymer C5 was synthesized by simple emulsion radical polymerization (nonsequential method).

TABLE 5

| Polymer tested | | Pol. 5 | C5 (outside the invention) |
|---|---|---|---|
| Composition P1 | EA | 55.92 | 60.44 |
| | MAA | 35.00 | 30.91 |
| | AM | 8.19 | 7.80 |
| | TMPTA | 0.89 | 0.85 |
| Composition P2 | EA | 72.50 | |
| | MAA | 20.00 | |
| | AM | 6.76 | |
| | TMPTA | 0.74 | |
| Overall composition | EA | 60.44 | 60.44 |
| | MAA | 30.91 | 30.91 |
| | AM | 7.80 | 7.80 |
| | TMPTA | 0.85 | 0.85 |
| | Proportion P1 | 72.74 | 100.00 |
| | Proportion P2 | 27.26 | 0.00 |
| 2.4% active agent, pH = 5 | Brook Visco (mPa·s) | 9,400 | 11,100 |
| | Suspension grade | 5 | 3 |
| | T (500 nm) (%) | 84 | 92 |

These results show that the use of a polymer with a multiphasic structure according to the invention, in comparison with a simple polymer, makes it possible to access improved suspensive performances of the formulation, while retaining satisfactory properties of viscosity and of transmittance.

Example 4

Influence of the Polymer P1/Polymer P2 Ratio

TABLE 6

| Polymer tested | | Pol. 6 | Pol. 7 | C6 (outside the invention) |
|---|---|---|---|---|
| Composition P1 | EA | 55.92 | 55.92 | 55.92 |
| | MAA | 35.00 | 35.00 | 35.00 |
| | AM | 8.19 | 8.19 | 8.19 |
| | TMPTA | 0.89 | 0.89 | 0.89 |
| Composition P2 | EA | 62.01 | 62.01 | 62.01 |
| | MAA | 30.50 | 30.49 | 30.50 |
| | AM | 6.76 | 6.76 | 6.76 |
| | TMPTA | 0.74 | 0.74 | 0.74 |
| Overall composition | EA | 57.58 | 58.17 | 60.46 |
| | MAA | 33.77 | 33.33 | 31.64 |
| | AM | 7.80 | 7.66 | 7.12 |
| | TMPTA | 0.85 | 0.83 | 0.78 |
| Proportion P1 | | 72.74 | 62.98 | 25.32 |
| Proportion P2 | | 27.26 | 37.02 | 74.68 |
| Brook Visco at 2% active agent (mPa·s) | pH = 4 | 9,300 | 8,500 | 7,600 |
| | pH = 5 | 8,000 | 7,200 | 6,300 |
| Suspension grade at 2% active agent | pH = 4 | 5 | 5 | 3 |
| | pH = 5 | 5 | 5 | 3 |
| T (500 nm) at 2% active agent (%) | pH = 4 | 84 | 83 | 87 |
| | pH = 5 | 83 | 84 | 87 |

The invention claimed is:

1. A multiphasic polymer, comprising from 45% to 95% by weight of a first polymer P1 and from 5% to 55% by weight of a second polymer P2, said polymers P1 and P2 being of distinct compositions, wherein:
   (1) the polymer P1 is obtained by polymerization from a mixture of monomers comprising:
   at least one anionic monomer (a) having a polymerizable vinyl group,
   at least one nonionic hydrophobic monomer (b) having a polymerizable vinyl group,
   at least one cross-linking monomer (c),
   at least one associative monomer (d) having a polymerizable vinyl group and a hydrophobic hydrocarbon chain, and
   optionally at least one additional nonionic monomer (e), distinct from the monomer (b); and (2) the polymer P2 is obtained by polymerization from a mixture of monomers comprising:
at least one anionic monomer (a') having a polymerizable vinyl group,
at least one nonionic hydrophobic monomer (b') having a polymerizable vinyl group,
at least one cross-linking monomer (c'),
optionally at least one associative monomer (d') having a polymerizable vinyl group and a hydrophobic hydrocarbon chain, and
optionally at least one additional nonionic monomer (e'), distinct from the monomer (b').

2. The polymer according to claim 1, wherein a polymer P1/polymer P2 weight ratio is between 45/55 and 95/5.

3. The polymer according to claim 1, wherein said anionic monomer(s) is(are) selected from the group consisting of a monomer of acrylic acid, a monomer of methacrylic acid, salts thereof and mixtures thereof.

4. The polymer according to claim 1, wherein said anionic monomer(s) (a) represent(s) from 20% to 53% by weight, based on a total weight of monomers constituting the polymer P1.

5. The polymer according to claim 1, wherein said anionic monomer(s) (a') represent(s) from 10% to 53% by weight, based on a total weight of monomers constituting the polymer P2.

6. The polymer according to claim 1, wherein said nonionic hydrophobic monomer(s) is(are) selected from the group consisting of a $C_1$-$C_8$ alkyl acrylate, a $C_1$-$C_8$ alkyl methacrylate, and mixtures thereof.

7. The polymer according to claim 1, wherein said nonionic hydrophobic monomer(s) (b) represent(s) from 40% to 75% by weight, based on a total weight of monomers constituting the polymer P1.

8. The polymer according to claim 1, wherein said nonionic hydrophobic monomer(s) (b') represent(s) from 50% to 85% by weight, based on a total weight of monomers constituting the polymer P2.

9. The polymer according to claim 1, wherein a nonionic hydrophobic monomers (b')/anionic monomers (a') weight ratio of the composition of the polymer P2 is between 60/40 and 85/15.

10. The polymer according to claim 1, wherein said cross-linking monomer(s) is(are) a trifunctional cross-linking monomer.

11. The polymer according to claim 1, wherein a content of cross-linking monomer(s) (c) in the composition of the polymer P1 is greater than or equal to 0.3% by weight, based on a total weight of the monomers constituting the polymer P1.

12. The polymer according to claim 1, wherein a content of cross-linking monomer(s) (c') in the composition of the polymer P2 is greater than or equal to 0.2% by weight, based on a total weight of the monomers constituting the polymer P2.

13. The polymer according to claim 1, wherein said associative monomer(s) is(are) monomers of following formula (I):

in which:
T represents an end which makes possible the copolymerization of the associative monomer;
$[(EO)_n(PO)_{n'}(BO)_{n''}]$ represents a polyalkoxylated chain consisting of alkoxylated units, distributed in blocks, alternating or random, selected from the group consisting of ethoxylated units EO, propoxylated units PO and butoxylated units BO;
n, n' and n" represent, independently of one another, 0 or an integer varying from 1 to 150; and
Z represents a linear or branched fatty chain of at least 12 carbon atoms and optionally comprising one or more 5- to 7-membered cyclic group(s) which are saturated, partially unsaturated or aromatic,
said groups may be optionally substituted.

14. The polymer according to claim 1, wherein said associative monomer(s) is(are) present in a proportion of at least 0.5% by weight, based on a total weight of monomers constituting the polymer P1.

15. The polymer according to claim 1, wherein the additional nonionic monomers (e) and (e') are selected from the group consisting of:
2-acrylamido-2-methylpropanesulfonic acid (AMPS),
an unsaturated telomer of acrylic acid,
a monomer of formula (e1):

in which:
$R_a$, $R_b$ and $R_c$ represent, independently of one another, H or $CH_3$,
n is an integer equal to 1 or 2, and
a monomer of formula (e2):

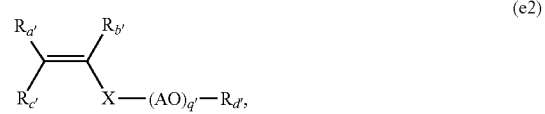

in which:
$R_{a'}$, $R_{b'}$, $R_{c'}$ and $R_{d'}$ represent, independently of one another, H or $CH_3$,
X represents (C=O) or $(CH_2)_r$ with r=0, 1 or 2,
(AO) represents a polyalkoxylated chain consisting of alkoxylated units, distributed in blocks, alternating or random, chosen from ethoxylated units EO, propoxylated units PO and butoxylated units BO, and
q represents 0 or an integer varying from 1 to 150.

16. The polymer according to claim 1, comprising:
(1) a polymer P1 obtained by polymerization from a mixture of monomers comprising:
from 30% to 43% by weight of at least one anionic monomer (a) having a polymerizable vinyl group,
from 50% to 65% by weight of at least one nonionic hydrophobic monomer (b) having a polymerizable vinyl group,
from 0.4% to 5% by weight of at least one cross-linking monomer (c),
at least 0.5% by weight of at least one associative monomer (d) having a polymerizable vinyl group and a hydrophobic hydrocarbon chain, and
optionally at least one additional nonionic monomer (e), distinct from the monomer (b); and (2) a polymer P2 obtained by polymerization from a mixture of monomers comprising, indeed even being constituted of:
- from 20% to 43% by weight of at least one anionic monomer (a') having a polymerizable vinyl group,
- from 60% to 75% by weight of at least one nonionic hydrophobic monomer (b') having a polymerizable vinyl group,
- from 0.3% to 5% by weight of at least one cross-linking monomer (c'),
- optionally at least one associative monomer (d') having a polymerizable vinyl group and a hydrophobic hydrocarbon chain, and
- optionally at least one additional nonionic monomer (e'), distinct from the monomer (b').

17. A method for preparing the multiphasic polymer of claim 1, the method comprising:
   (i) polymerizing the polymer P1 from a first mixture of monomers comprising:
   - at least one anionic monomer (a) having a polymerizable vinyl group,
   - at least one nonionic hydrophobic monomer (b) having a polymerizable vinyl group,
   - at least one cross-linking monomer (c),
   - at least one associative monomer (d) having a polymerizable vinyl group and a hydrophobic hydrocarbon chain, and
   - optionally at least one additional nonionic monomer (e), distinct from the monomer (b); and
   (ii) polymerizing, in the presence of the polymer P1 obtained above, a second mixture of monomers comprising:
   - at least one anionic monomer (a') having a polymerizable vinyl group,
   - at least one nonionic hydrophobic monomer (b') having a polymerizable vinyl group,
   - at least one cross-linking monomer (c'),
   - optionally an associative monomer (d') having a polymerizable vinyl group and a hydrophobic hydrocarbon chain, and
   - optionally at least one additional nonionic monomer (e'), distinct from the monomer (b').

18. An aqueous composition, comprising at least one multiphasic polymer of claim 1.

19. The composition according to claim 18, having a pH value of less than or equal to 6.

20. The composition according to claim 18, comprising from 0.1% to 20% by weight of the multiphasic polymer(s) based on its total weight.

21. A thickening or suspending agent, comprising the multiphasic polymer of claim 1.

* * * * *